United States Patent
Aspnes

(10) Patent No.: US 7,355,708 B2
(45) Date of Patent: *Apr. 8, 2008

(54) NORMAL INCIDENCE ROTATING COMPENSATOR ELLIPSOMETER

(75) Inventor: David E. Aspnes, Apex, NC (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/638,023

(22) Filed: Dec. 13, 2006

(65) Prior Publication Data
US 2007/0091311 A1    Apr. 26, 2007

Related U.S. Application Data

(63) Continuation of application No. 10/840,443, filed on May 6, 2004, now Pat. No. 7,173,700.

(51) Int. Cl.
*G01J 4/00*    (2006.01)
(52) U.S. Cl. ................................. 356/369
(58) Field of Classification Search ............ None
See application file for complete search history.

(56) References Cited

U.S. PATENT DOCUMENTS

| | | | |
|---|---|---|---|
| 5,739,909 A | 4/1998 | Blayo et al. ............ 356/369 |
| 5,798,837 A | 8/1998 | Aspnes et al. ............ 356/369 |
| 5,872,630 A | 2/1999 | Johs et al. ............ 356/369 |
| 5,910,842 A | 6/1999 | Piwonka-Corle et al. ... 356/369 |
| 6,429,943 B1 | 8/2002 | Opsal et al. ............ 356/625 |
| 6,449,043 B2 * | 9/2002 | Aspnes et al. ............ 356/369 |
| 6,456,376 B1 | 9/2002 | Liphardt et al. ............ 356/369 |
| 6,583,875 B1 | 6/2003 | Wei et al. ............ 356/369 |
| 6,665,070 B1 | 12/2003 | Yarussi et al. ............ 356/369 |
| 6,713,753 B1 | 3/2004 | Rovira et al. ............ 250/225 |
| 6,934,025 B2 | 8/2005 | Opsal et al. ............ 356/369 |
| 6,982,791 B2 | 1/2006 | Opsal ............ 356/369 |
| 7,054,006 B2 | 5/2006 | Wang et al. ............ 356/369 |

OTHER PUBLICATIONS

R.M.A. Azzam, "PIE: Perpendicular-Incidence Ellipsometry—Application to the Determination of the Optical Properties of Uniaxial and Biaxial Absorbing Crystals," *Optics Communications*, vol. 19. No. 1, Oct. 1976, pp. 122-124.

R.M.A. Azzam, "NIRSE: Normal-Incidence Rotating-Sample Ellipsometer," *Optics Communications*, vol. 20, No. 3, Mar. 1977, pp. 405-408.

(Continued)

*Primary Examiner*—Tu T Nguyen
(74) *Attorney, Agent, or Firm*—Stallman & Pollock LLP

(57) ABSTRACT

A normal incidence rotating compensator ellipsometer includes an illumination source that produces a broadband probe beam. The probe beam is redirected by a beam splitter to be normally incident on a sample under test. Before reaching the sample, the probe beam is passed through a rotating compensator. The probe beam is reflected by the sample and passes through the rotating compensator a second time before reaching a detector. The detector converts the reflected probe beam into equivalent signals for analysis.

20 Claims, 2 Drawing Sheets

OTHER PUBLICATIONS

R.M.A. Azzam, "Perpendicular-incidence null ellipsometry of surfaces with arbitrary anisotropy," *Optical Engineering*, vol. 20, No. 1, Jan./Feb. 1981, pp. 58-61.

J.M Holden et al., "Normal Incidence Spectroscopic Ellipsometry and Polarized Reflectometry for Measurement of Photoresist Critical Dimensions," *Proceedings of SPIE (Metrology, Inspection, and Process Control for Microlithography XVI)*, vol. 4689 (2002), pp. 1110-1121.

H.-T. Huang et al., "Normal-incidence spectroscopic ellipsometry for critical dimension monitoring," *Applied Physics Letters*, vol. 27, No. 25, Jun. 18, 2001, pp. 3983-3985.

H. Fu et al., "Retroreflecting ellipsometer for measuring the birefringence of optical disk substrates," *Applied Optics*, vol. 34, No. 1, Jan. 1, 1995, pp. 31-39.

Y. Cui et al., "Applications of the normal-incidence rotating-sample ellipsometer to high- and low-spatial-frequency gratings," *Applied Optics*, vol. 35, No. 13, May 1, 1996, pp. 2235-2238.

O. Acher et al., "A reflectance anisotropy spectrometer for real-time measurements," *Rev. Sci. Instrum*, vol. 63, No. 11, Nov. 1992, pp. 5332-5339.

R.M.A. Azzam, "Return-path ellipsometry and a novel normal-incidence null ellipsometer (NINE)," *Optical Acta*, vol. 24, No. 10 (1997), pp. 1039-1049.

R.M.A. Azzam, "Perpendicular-Incidence Photometric Ellipsometry (PIPE) of Surfaces with Arbitrary Anisotropy," *J. Optics (Paris)*, vol. 12, No. 5 (1981), pp. 317-321.

* cited by examiner

NORMAL INCIDENCE ROTATING COMPENSATOR ELLIPSOMETER

PRIORITY

This application is a continuation of U.S. patent application Ser. No. 10/840,443, filed May 6, 2004, now U.S. Pat. No. 7,173,700.

TECHNICAL FIELD

The subject invention relates to optical devices used to non-destructively evaluate semiconductor wafers. In particular, the present invention relates to increasing the accuracy of normal incidence metrology systems.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed. Ellipsometry and reflectometry are effective methods for measuring a wide range of attributes including information about thickness, crystallinity, composition and refractive index. The structural details of ellipsometers are more fully described in U.S. Pat. Nos. 6,449,043, 5,910,842 and 5,798,837 each of which are incorporated in this document by reference.

Scatterometry is a specific type of optical metrology that is used when the structural geometry of a subject creates diffraction (optical scattering) of the incoming probe beam. Scatterometry systems analyze diffraction to deduce details of the structures that cause the diffraction to occur. Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry, in these cases generally refers to optical responses in the form of diffraction orders produced by periodic structures, that is, gratings on the wafer. In addition it may be possible to employ any of these measurement technologies, e.g., single-wavelength laser BPR or BPE, to obtain critical dimension (CD) measurements on non-periodic structures, such as isolated lines or isolated vias and mesas. The above cited patents and patent applications, along with PCT Application No. WO 03/009063, U.S. application Ser. No. 2002/0158193, U.S. application Ser. No. 2003/0147086, U.S. application Ser. No. 2001/0051856 A1, PCT Application No. WO 01/55669 and PCT Application No. WO 01/97280 are all incorporated herein by reference.

Normal incidence ellipsometry is a widely used type of optical metrology, both for thin film measurements as well as scatterometry applications. As shown in FIG. 1, an instrument of this type includes an illumination source that typically produces a broadband polychromatic probe beam. The probe beam is directed by one or more refractive or reflective components (represented as a lens in this example) to a beam splitter. The beam splitter redirects the probe beam through a rotating polarizer and objective lens (which is typically composed of a series of reflective and/or refractive components) before reaching a sample under test. The sample reflects the probe beam and a portion of the reflected probe beam is captured by the objective. The reflected probe beam then passes through the rotating polarizer and beam splitter and is directed by one or more refractive or reflective components (represented, again, as a lens) to a spectrometer. The spectrometer converts the probe beam into equivalent signals for analysis by a processor.

For the situation where a grating is being measured by normal-incidence reflectance, the grating is typically oriented so the rulings (grooves) are either parallel or perpendicular to the electric field emerging from the polarizer. These are the two normal modes of the system, where linearly polarized light incident on the grating is reflected as linearly polarized light. The mode where the incident/reflected electric field is parallel to the rulings is conventionally denoted as the transverse magnetic (TM) mode. The other normal mode, where the electric field vector is perpendicular to the rulings, is conventionally denoted the transverse electric (TE) mode. Reflectance measurements using these two modes allow the absolute squares $R_a=|r_a|^2$ and $R_b=|r_b|^2$ of the complex reflectances $r_a$ and $r_b$ for electric fields parallel and perpendicular, respectively, to the rulings to be determined.

More general normal-incidence reflectance measurements are also possible. The field vector does not need to be oriented as described above, but can assume any azimuth angle P relative to the rulings. Typically, this angle is varied by rotating the polarizer, although it can be varied by rotating either the polarizer or the grating, either at a fixed angular velocity or as a series of discrete steps. At intermediate angles $$P \neq n\frac{\pi}{2},$$

where n is an integer, the two modes are mixed. This allows the relative amplitude and phase of $r_a$ and $r_b$ to be determined. Specifically, the intensity of the reflected probe beam as a general function of P can be written $$I(P)=\alpha_0+\alpha_2 \cos(2P)+\alpha_4 \cos(4P)$$

where the Fourier coefficients $\alpha_0$, $\alpha_2$, and $\alpha_4$ are given by $$a_0 = \frac{3}{8}(|r_a|^2 + |r_b|^2) + \frac{1}{4}\text{Re}(r_a r_b^*);$$

$$a_2 = \frac{1}{2}(|r_a|^2 - |r_b|^2);$$

$$a_4 = \frac{1}{8}(|r_a|^2 + |r_b|^2) - \frac{1}{4}\text{Re}(r_a r_b^*).$$

This calculation assumes that at P=0 the electric field is parallel to the rulings, and ignores the partial polarization that would be caused by the beam splitter sketched in FIG. 1.

As can be seen, rotating the polarizer generates an additional perspective ($\text{Re}(r_a r_b^*)$). However, the rotating polarizer design is unable to measure the complementary quantity, the imaginary component $\text{Im}(r_a r_b^*)$. In addition, if the polarizer is rotated, partial polarization of the source or polarization sensitivity of the detector can lead to systematic errors that cannot be distinguished from the signal due to the sample. Finally, the configuration provides no intrinsic way of verifying that the rulings are indeed parallel to the electric field vector when P is nominally equal to zero.

The inability to measure $\text{Im}(r_a r_b^*)$ is also true of non-normally incident ellipsometers that utilize single rotating compensators. $\text{Im}(r_a r_b^*)$ may be obtained by non-normally incident designs that include modulators in both incident and reflected beams. Designs of this type are obviously more complex (since they include multiple photoelastic-modulators or multiple rotating compensators) and are unable to achieve the small spot sizes available to normal incidence designs. Consequently, there are reasons to believe that measurement accuracy may be improved by other designs that do not suffer these limitations.

SUMMARY

An embodiment of the present invention provides a normal incidence ellipsometer for scatterometry applications. A typical implementation for an ellipsometer of this type includes an illumination source that produces a broadband white-light probe beam. A polarizer is used to impart a known polarization state to the probe beam. The probe beam is then directed through a rotating compensator that introduces a relative phase delay $\xi$ (phase retardation) between a pair of mutually orthogonally polarized components of the probe beam. After leaving the compensator, the probe beam is directed at normal incidence against the surface of the sample. The sample reflects the probe beam back through the compensator and on to a second polarizer (also referred to as an analyzer). A detector measures the intensity of the probe beam leaving the analyzer as a function of rotational angle of the compensator or analyzer.

A processor analyzes the output of the detector to obtain the quantities: $|r_a|^2$, $|r_b|^2$, $\text{Re}(r_a r_b^*)$, and $\text{Im}(r_a r_b^*)$. This surpasses traditional rotating polarizer designs that are unable to measure the imaginary component $\text{Im}(r_a r_b^*)$. It should also be noted that the measured quantities are obtained without the need to align gratings within the sample relative to the polarization of the probe beam.

DETAILED DESCRIPTION OF THE PREFERRED EMBODIMENTS

Figure 1:
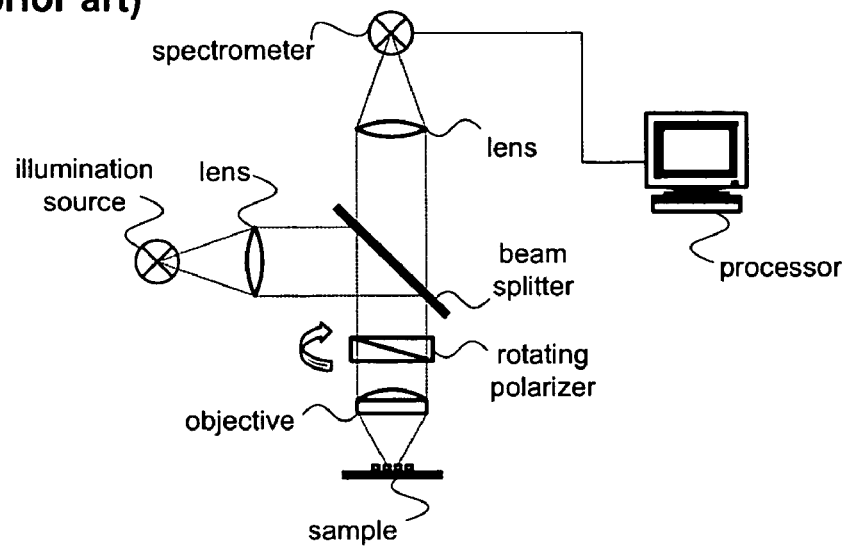
FIG. 1 shows a prior art ellipsometer that includes a rotating polarizer.
Figure 2:
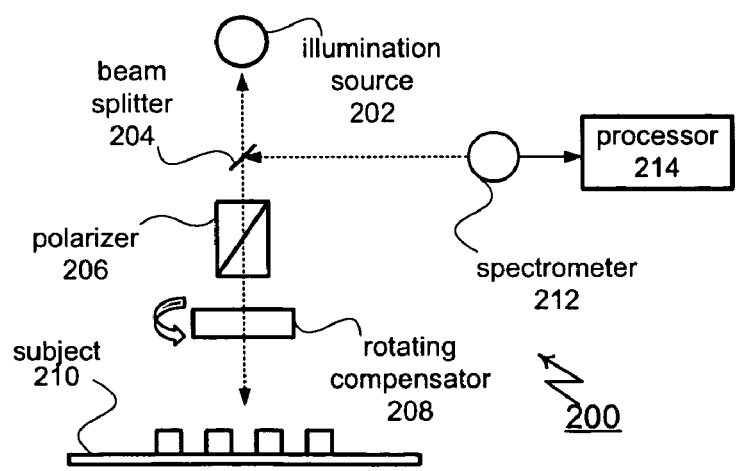
FIGS. 2 through 4 show different implementations of the normal incidence rotating compensator ellipsometer provided by the present invention.

An embodiment of the present invention provides a normal incidence ellipsometer for scatterometry applications. As shown in FIG. 2, a first implementation for the normal incidence ellipsometer 200 includes an illumination source 202. Illumination source 202 produces a broadband white-light probe beam that is projected through a beam splitter 204, polarizer 206 and rotating compensator 208 before reaching a subject 210. As it traverses this path, polarizer 206 imparts a known polarization state to the probe beam. Rotating compensator 208 introduces a relative phase delay $\xi$ (phase retardation) between a pair of mutually orthogonally polarized optical beam components. The amount of phase retardation is a function of the wavelength, the dispersion characteristics of the material used to form compensator 208, and the thickness of the compensator 208. Compensator 208 is rotated at an angular velocity $\omega$ about an axis substantially parallel to the propagation direction of the probe beam. When used in this document, rotation is intended to include continuous rotation, as well as rotation in increments or steps. Subject 210 returns the probe beam (though polarizer 206 and rotating compensator 208) to beam splitter 204. Beam splitter 204 redirects the returning probe beam to a spectrometer 212. Spectrometer 212 is typically a monochrometer-CCD detector combination, but other technologies can also be used.

Figure 3:
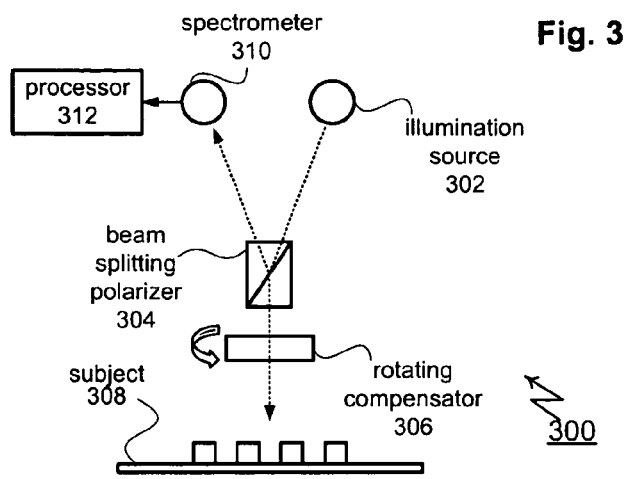

FIG. 3 shows a second implementation 300 for the normal incidence ellipsometer. Ellipsometer 300 shares many of the components described for ellipsometer 200 with the main difference being that the beam splitter 204 and polarizer 206 have been replaced by a beam splitting polarizer 304. Beam splitting polarizer 304 is a Wollaston prism and performs two functions. The first is to impart a known polarization state to the probe beam. The second is to function as a beam splitter/combiner. As the probe beam returns from subject 308, beam splitting polarizer 304 directs a portion of the returning probe beam to spectrometer 310.

Figure 4:
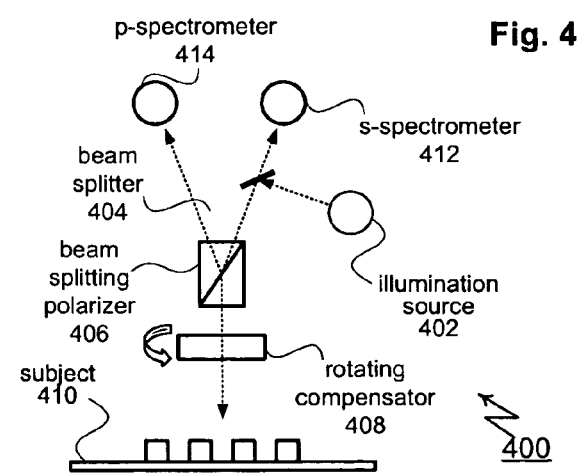

As shown in FIG. 4, a third implementation for the normal incidence ellipsometer 400 includes an illumination source 402. Illumination source 402 produces a broadband white-light probe beam that is projected through a beam splitter 404, beam splitting polarizer 406 and rotating compensator 408 before reaching a subject 410. As it traverses this path, polarizer 406 imparts a known polarization state to the probe beam. Rotating compensator 408 introduces a relative phase delay $\xi$ between a pair of mutually orthogonally polarized optical beam components. The amount of phase retardation is a function of the wavelength, the dispersion characteristics of the material used to form compensator 408, and the thickness of the compensator 408. Compensator 408 is rotated at an angular velocity $\omega$ about an axis substantially parallel to the propagation direction of the probe beam. When used in this document, rotation is intended to include continuous rotation, as well as rotation in increments or steps. Subject 410 returns the probe beam (though polarizer 406 and rotating compensator 408) to beam splitter 404.

Beam splitting polarizer 406 is a Wollaston prism and performs two functions. The first is to impart a known polarization state to the probe beam. The second is to function as a beam splitter/combiner. As the probe beam returns from subject 410, beam splitting polarizer 406 splits the returning probe beam into two components. The first component (referred to as s-polarized) is characterized by having detected polarization is identical with that of the illuminating polarization, and is directed to s-spectrometer 412. The orthogonally polarized return component is denoted p-polarized, and is directed to p-spectrometer 414. Spectrometer 412 and 414 are typically monochrometer-CCD detector combinations, but other technologies can also be used.

The intensity of the reflected probe beam received by spectrometers 412 and 414 is a function of the azimuth angle of the rotating compensator 408 relative to the electric field vector and the grating rulings. In what follows C is defined to be the azimuth angle locating the fast axis of the compensator relative to the azimuth angle of the polarizer, which is taken as reference, i.e., to define the value C=0°. The second azimuth angle that must be defined is that of the rulings relative to the same reference as C. The second azimuth angle is denoted as G, where G=0° is the condition where the rulings of the grating are parallel to the field emerging from the polarizer.

For arbitrary G, I(C) has the general form:

$$I(C) = a_0 + a_2\cos(2C) + b_2\sin(2C) + a_4\cos(4C) + b_4\sin(4C) + a_6\cos(6C) + b_6\sin(6C) + a_8\cos(8C) + b_8\sin(8C).$$

However, for G=0° none of the sin(nC) terms are present, and the general coefficients (to be given later below) simplify. For s-spectrometer 412, this yields:

$$a_0^{(s)} = |r_a|^2\left[\cos^4\frac{\xi}{2} + \frac{1}{4}\sin^2\xi + \frac{3}{8}\sin^4\frac{\xi}{2}\right] + |r_b|^2\left[\frac{3}{8}\sin^4\frac{\xi}{2}\right] + \text{Re}(r_a r_b^*)\left[\frac{1}{4}\sin^4\frac{\xi}{2} - \frac{1}{4}\sin^2\xi\right]$$

$$a_2^{(s)} = \text{Im}(r_a r_b^*)\left[-\frac{1}{2}\sin\xi\sin^2\frac{\xi}{2}\right]$$

$$a_4^{(s)} = |r_a|^2\left[\frac{1}{4}\sin^2\xi + \frac{1}{2}\sin^4\frac{\xi}{2}\right] + |r_b|^2\left[-\frac{1}{2}\sin^4\frac{\xi}{2}\right] + \text{Re}(r_a r_b^*)\left[\frac{1}{4}\sin^2\xi\right]$$

$$a_6^{(s)} = \text{Im}(r_a r_b^*)\left[\frac{1}{2}\sin\xi\sin^2\frac{\xi}{2}\right]$$

$$a_8^{(s)} = [|r_a|^2 + |r_b|^2]\left[\frac{1}{8}\sin^4\frac{\xi}{2}\right] + \text{Re}(r_a r_b^*)\left[-\frac{1}{4}\sin^4\frac{\xi}{2}\right]$$

where $\xi = 2\pi d(n_e - n_o)/\lambda$, where d is the effective thickness of the compensator $n_o$ and $n_e$ are refractive indices of the ordinary and extraordinary polarizations in the compensator, and $\lambda$ is the wavelength of light. For p-spectrometer 414 the corresponding expressions are:

$$a_0^{(p)} = [|r_a|^2 + |r_b|^2]\left[\frac{1}{8}\sin^4\frac{\xi}{2} + \frac{1}{8}\sin^4\xi\right] + \text{Re}(r_a r_b^*)\left[-\frac{1}{4}\sin^4\frac{\xi}{2} + \frac{1}{4}\sin^4\xi\right]$$

$$a_2^{(s)} = \text{Im}(r_a r_b^*)\left[\frac{1}{2}\sin^2\frac{\xi}{2}\sin\xi\right]$$

$$a_4^{(p)} = [|r_a|^2 + |r_b|^2]\left[-\frac{1}{8}\sin^2\xi\right] + \text{Re}(r_a r_b^*)\left[-\frac{1}{4}\sin^2\xi\right]$$

$$a_6^{(s)} = \text{Im}(r_a r_b^*)\left[-\frac{1}{2}\sin^2\frac{\xi}{2}\sin\xi\right]$$

$$a_8^{(s)} = [|r_a|^2 + |r_b|^2]\left[-\frac{1}{8}\sin^4\frac{\xi}{2}\right] + \text{Re}(r_a r_b^*)\left[\frac{1}{4}\sin^4\frac{\xi}{2}\right]$$

where again max $(a_0^{(s)}) = \frac{1}{2}$.

This is a total of five distinct nonzero Fourier coefficients for both spectrometers 412 and 414. Given $\xi$, for either set of coefficients the sample parameters $|r_a|^2, |r_b|^2, \text{Re}(r_a r_b^*)$ and $\text{Im}(r_a r_b^*)$ are overdetermined. However, their most probable values can be obtained by least-squares fitting. Least-squares routines have the added advantages that (a) the coefficients that are most important in determining a given parameter are also given the most weight; and (b) a measure of the capability of the system to determine all parameters is provided by the goodness of fit. In fact unless absolute intensities are measured, which is hardly ever the case, the sample parameters are determined only to within a normalization constant, meaning that only three of the four sample parameters provide relevant sample information. However, this can be compared to the analogous situation without the compensator, where only two of the three parameters provide relevant information.

Once obtained, these parameters may be used in turn to estimate other sample parameters such as thickness of the grating, top and bottom line widths, and the thickness of an underlying film. As described previously, ellipsometers 200 and 300 include a single spectrometer (212 and 310, respectively). For the typical case, these spectrometers measure the s-polarized component of the reflected probe beam and are characterized by the first set of Fourier coefficients listed above. Alternately, spectrometers 212 and 310 may be configured to measure the p-polarization component described by the second set of five Fourier coefficients.

We now consider the situation where G takes on general values, so the rulings are not aligned either parallel or perpendicular to the electric field vector emerging from the polarizer. In this case the s-spectrometer receives an intensity whose Fourier components are:

DC terms:

$$\frac{3}{8}[|r_a|^2 + |r_b|^2]\sin^4\frac{\xi}{2} + [|r_a|^2\cos^4 G + |r_b|^2\sin^4 G]\left[\cos^4\frac{\xi}{2} + \frac{1}{4}\sin^4\xi\right] + \text{Re}(r_a r_b^*)\left[\frac{1}{4}\sin^2\frac{\xi}{2} + \frac{1}{2}\cos^4\frac{\xi}{2}\sin^2 2G - \frac{1}{4}\sin^2\xi\right]$$

2C' terms:

$$\text{Im}(r_a r_b^*)\left[\sin\xi\left(-\frac{1}{2}\sin^2\frac{\xi}{2}\cos(2C' - G) + \cos^2\frac{\xi}{2}\sin 2G \sin(2C' + G)\right)\right];$$

4C' terms:

$$\left\{\frac{1}{2}[|r_a|^2 - |r_b|^2]\sin^4\frac{\xi}{2} + \frac{1}{4}\sin^2\xi[|r_a|^2\cos^2 G - |r_b|^2\sin^2 G]\right\}\cos 4C' + \frac{1}{4}\text{Re}(r_a r_b^*)\sin^2\xi[\cos 2G\cos 4C' - 2\sin 2G\sin 4C'];$$

6C' terms:

$$\frac{1}{2}\text{Im}(r_a r_b^*)\sin\xi\sin^2\frac{\xi}{2}\cos(6C' + G);$$

8C' terms:

$$\frac{1}{8}[|r_a|^2 + |r_b|^2 - 2\text{Re}(r_a r_b^*)]\sin^4\frac{\xi}{2}\cos 8C';$$

where $$C' = C - \frac{G}{2}.$$

The p-spectrometer receives an intensity whose Fourier components are:

DC terms:

$$\frac{1}{8}[|r_a|^2 + |r_b|^2]\left[\sin^4\frac{\xi}{2} + 2\cos^4\frac{\xi}{2}\sin^2 2G + \sin^2\xi\right] - \frac{1}{4}\operatorname{Re}(r_a r_b^*)\left[\sin^2\frac{\xi}{2} + 2\cos^4\frac{\xi}{2}\sin^2 2G - \sin^2\xi\right];$$

2C' terms:

$$\operatorname{Im}(r_a r_b^*)\sin\xi\left[\frac{1}{2}\sin^2\frac{\xi}{2}\cos(2C' - G) - \cos^2\frac{\xi}{2}\sin 2G \sin(2C' + G)\right];$$

4C' terms:

$$-\frac{1}{8}\sin^2\xi[|r_a|^2 + |r_b|^2 + 2\operatorname{Re}(r_a r_b^*)]\cos 2G \cos 4C' + \frac{1}{2}\operatorname{Re}(r_a r_b^*)\sin^2\xi\sin 2G \sin 4C';$$

6C' terms:

$$-\frac{1}{2}\operatorname{Im}(r_a r_b^*)\sin\xi\sin^2\frac{\xi}{2}\cos(6C' + G);$$

8C' terms:

$$-\frac{1}{8}[|r_a|^2 + |r_b|^2 - 2\operatorname{Re}(r_a r_b^*)]\sin^4\frac{\xi}{2}\cos 8C'.$$

where $$C' = C - \frac{G}{2}.$$

It is now seen that there are in general nine coefficients available for analysis. We therefore obtain even further constraints on the sample parameters. In fact these overdetermine the four sample parameters $\operatorname{Re}(r_a r_b^*)$, and $\operatorname{Im}(r_a r_b^*)$. In addition we have enough information to determine G. Therefore, one of the main advantages of the configuration follows: it is not necessary to position the grating prior to measurement at G=0, but G can be determined from the coefficients themselves. Thus measurements can be made with an arbitrary orientation of the grating.

Extracting Reflectance Parameters at Normal Incidence (a) assume a sample with the principal axes a and b in the plane of the surface with field reflectances $r_a$ and $r_b$ for light polarized parallel to a and b respectively. We seek to obtain the four quantities:

$|r_a|^2, |r_b|^2, \operatorname{Re}(r_a r_b^*),$ and $\operatorname{Im}(r_a r_b^*)$.

For a series of measurements taken as a function of polarizer or compensator angle θ the intensity may be written (as shown above) as:

$$I_\omega = |r_a|^2 f_1(\theta) + |r_b|^2 f_2(\theta) + [\operatorname{Re}(r_a r_b^*)]f_3(\theta) + [\operatorname{Im}(r_a r_b^*)]f_4(\theta).$$

The functions $f_1 \ldots f_4$ could be reduced to their Fourier components but this is not necessary.

(b) Now calculate the elements $m_{ij}$ of the correlation matrix $M_1$ as:

$$m_{ij} = \frac{1}{N}\sum_{\omega=1}^{N} f_i(\theta_\omega)f_j(\theta_\omega)$$

and the elements $v_i$ of the weighted-intensity vector $V_1$ as:

$$v_i = \frac{1}{N}\sum_{\omega=1}^{N} I_\omega f_i(\theta_\omega)$$

where $\theta_\omega$ are the azimuth angles where the $I_\omega$ are recorded. Then if we make a vector A such that $a_1=|r_a|^2$, $\alpha_2=|r_b|^2$, $\alpha_3=\operatorname{Re}(r_a r_b^*)$, and $\alpha_4=\operatorname{Im}(r_a r_b^*)$ it follows that $$V = MA$$

and $$A = M^{-1}V$$

and so we have formally solved the problem of obtaining the four quantities from the intensity measurements. Note that it is not necessary to decomposed, $f_1 \ldots f_4$ into Fourier components. This approach may yield faster analysis in repetitive measurements.

What is claimed is:

1. An ellipsometer for evaluating a sample comprising:
   a broadband light source for generating a polychromatic probe beam;
   optics for directing the probe beam towards the sample at normal incidence along an illumination path and for collecting the probe beam after reflection from the sample along a collection path and wherein the illumination and collection paths at least partially overlap;
   a polarizer located in the illumination path for polarizing the probe beam;
   a rotating compensator located in the overlapping portion of the beam path so that the beam passes through the compensator in both the illumination and collection paths; and
   a spectrometer for measuring the intensity of the probe beam after reflection from the sample and generating output signals as a function of wavelength and rotational angle of the compensator.

2. An ellipsometer as recited in claim 1, wherein the probe beam passes though the polarizer in both paths.

3. An ellipsometer as recited in claim 1, wherein the probe beam is focused onto the sample with an objective lens.

4. An ellipsometer as recited in claim 1, further including a processor for analyzing the output signals.

5. An ellipsometer as recited in claim 4, wherein the sample includes surface features having critical dimensions and the processor evaluates the critical dimensions of the features.

6. An ellipsometer as recited in claim 5, wherein the features define a periodic structure.

7. An ellipsometer as recited in claim 6, wherein the periodic structure is a grating and wherein the grating is analyzed without aligning the grating relative to the polarization direction of the probe beam.

8. An ellipsometer as recited in claim 5, wherein the features are non-periodic.

9. A method for evaluating a sample comprising the steps of:
   generating a broadband, polychromatic probe beam;
   polarizing the probe beam;
   directing the probe beam towards the sample at normal incidence along an illumination path;
   collecting the probe beam after reflection from the sample along a collection path and wherein the illumination and collection paths at least partially overlap;
   passing the probe beam through a rotating compensator in both the illumination and collection paths; and
   measuring the intensity of the probe beam after reflection from the sample and generating output signals as a function of wavelength and rotational angle of the compensator, said output signals for evaluating the sample.

10. A method as recited in claim 9, wherein the probe beam is focused onto the sample with an objective lens.

11. A method as recited in claim 9, wherein the sample includes surface features having critical dimensions and further including the step of evaluating the critical dimensions of the features.

12. A method as recited in claim 11, wherein the features define a periodic structure.

13. A method as recited in claim 12, wherein the periodic structure is a grating and wherein the grating is analyzed without aligning the grating relative to the polarization direction of the probe beam.

14. A method as recited in claim 11, wherein the features are non-periodic.

15. An ellipsometer for evaluating a sample comprising:
   a broad band light source for generating a polychromatic probe beam;
   optics for directing the probe beam towards the sample along an illumination path at normal incidence;
   a spectrometer for measuring the intensity of the probe beam after reflection along a collection path from the sample and generating output signals as a function of wavelength and wherein the illumination and collection paths at least partially overlap; and
   a polarizer located in the beam path between light source and the spectrometer; and
   a rotating compensator located in the overlapping portion of the beam path between the light source and the spectrometer so that the beam passes through the compensator twice.

16. An ellipsometer as recited in claim 15, wherein the probe beam is focused onto the sample with an objective lens.

17. An ellipsometer as recited in claim 15, further including a processor for analyzing the output signals.

18. An ellipsometer as recited in claim 17, wherein the sample includes surface features having critical dimensions and the processor evaluates the critical dimensions of the features.

19. An ellipsometer as recited in claim 18, wherein the features define a periodic grating and wherein the grating is analyzed without aligning the grating relative to the polarization direction of the probe beam.

20. An ellipsometer as recited in claim 18, wherein the features are non-periodic.

* * * * *